(12) United States Patent
Agace

(10) Patent No.: US 8,884,259 B2
(45) Date of Patent: Nov. 11, 2014

(54) SYSTEM AND METHOD FOR TRANSFERRING AND/OR WORKING NEAR A RADIOACTIVE PAYLOAD USING SHIELD-GATE APPARATUS

(75) Inventor: Stephen J. Agace, Marlton, NJ (US)

(73) Assignee: Holtec International, Inc.

( * ) Notice: Subject to any disclaimer, the term of this patent is extended or adjusted under 35 U.S.C. 154(b) by 0 days.

(21) Appl. No.: 14/118,848

(22) PCT Filed: May 21, 2012

(86) PCT No.: PCT/US2012/038898
§ 371 (c)(1),
(2), (4) Date: Nov. 19, 2013

(87) PCT Pub. No.: WO2012/159119
PCT Pub. Date: Nov. 22, 2012

(65) Prior Publication Data
US 2014/0070118 A1    Mar. 13, 2014

Related U.S. Application Data

(60) Provisional application No. 61/487,823, filed on May 19, 2011.

(51) Int. Cl.
| G21F 5/00 | (2006.01) |
| G21F 7/005 | (2006.01) |
| G21F 5/12 | (2006.01) |
| G21F 5/14 | (2006.01) |

(52) U.S. Cl.
CPC ... *G21F 5/12* (2013.01); *G21F 5/14* (2013.01); *G21F 7/005* (2013.01)
USPC .................. 250/507.1; 250/506.1; 250/515.1

(58) Field of Classification Search
USPC ...................................................... 250/507.1
See application file for complete search history.

(56) References Cited

U.S. PATENT DOCUMENTS

| 3,149,045 A | 9/1964 | Boyd et al. |
| 3,175,854 A | 3/1965 | Lee et al. |
| 3,629,062 A | 12/1971 | Muenchow |
| 3,739,451 A | 6/1973 | Jacobson |
| 3,836,267 A | 9/1974 | Schatz |
| 4,158,599 A | 6/1979 | Andrews et al. |
| 4,288,698 A | 9/1981 | Baatz et al. |
| 4,355,000 A | 10/1982 | Lumelleau |
| 4,483,205 A * | 11/1984 | Bellaiche et al. .......... 73/863.23 |
| 4,526,344 A | 7/1985 | Oswald et al. |

(Continued)

FOREIGN PATENT DOCUMENTS

GB    1306806    2/1973

*Primary Examiner* — Phillip A Johnston
(74) *Attorney, Agent, or Firm* — The Belles Group, P.C.

(57) ABSTRACT

A system and method of transferring a radioactive payload using a shield-gate apparatus, including a method of performing work within a cavity of a shielding container using a shield-gate apparatus and shielding block, in one embodiment, the invention is a system comprising: a shield-gate apparatus comprising a body, a passageway extending along an axis through the body, and one or more movable shielding gates; a shielding block positioned atop the body of the shield-gate apparatus to enclose a first opening of the passageway; and a retaining feature that prevents relative transverse movement between the shielding block and the shield-gate apparatus while allowing relative rotation between the shielding block and the shield-gate apparatus about a central axis of the shielding block.

20 Claims, 19 Drawing Sheets

(56) References Cited

U.S. PATENT DOCUMENTS

| | | |
|---|---|---|
| 4,764,333 A | 8/1988 | Minshall et al. |
| 5,319,686 A * | 6/1994 | Pizzano et al. ............... 376/272 |
| 5,513,231 A | 4/1996 | Jones et al. |
| 5,546,436 A | 8/1996 | Jones et al. |
| 5,633,904 A | 5/1997 | Gilligan, III et al. |
| 5,641,970 A | 6/1997 | Taniuchi et al. |
| 5,661,768 A * | 8/1997 | Gilligan et al. ............... 376/261 |
| 6,064,710 A | 5/2000 | Singh |
| 6,625,246 B1 | 9/2003 | Singh et al. |
| 2005/0157833 A1 | 7/2005 | Ishihara et al. |
| 2009/0123255 A1 | 5/2009 | Waisanen |
| 2011/0042586 A1 | 2/2011 | Liu et al. |

* cited by examiner

SYSTEM AND METHOD FOR TRANSFERRING AND/OR WORKING NEAR A RADIOACTIVE PAYLOAD USING SHIELD-GATE APPARATUS

CROSS-REFERENCE TO RELATED PATENT APPLICATIONS

This application claims the benefit of U.S. Provisional Patent Application No. 61/487,823, filed May 19, 2011, the entirety of which is incorporated herein by reference.

FIELD OF THE INVENTION

The present invention relates generally to systems and methods of handling and/or working near radioactive payloads, and specifically to system and methods of transferring and/or working near radioactive payloads using a shield-gate structure.

BACKGROUND OF IDE INVENTION

During the handling and/or working near radioactive waste, such as high level radioactive which includes spent nuclear fuel, it is important that the radioactive payload be shielded from the external environment to the maximum extent possible to protect both the environment and nearby workers. Radioactive payloads include filters, spent nuclear fuel rods, vitrified waste, and other forms of both high level and low level radioactive materials. Providing adequate shielding for the radioactive payload becomes especially challenging when the radioactive payload either needs to be transferred from one shielding container to another shielding container and/or when work nears to be performed near said radioactive payload. In instances of transfer, the potential danger of radiation shine is prevalent not only when the radioactive payload is being physically moved from the one shielding container to the other shielding container, but also when the removable lids of the various containment structures have to be removed to access the cavity in which the radioactive payload is situated. In instances of work, the danger of substantial radiation shine is also prevalent due to the creation of openings and other access passageways that are necessarily created so that various tools can be inserted into the cavity from the external atmosphere for performing the desired work.

Efforts have been made to introduce mating devices that minimize radiation shine during spent nuclear fuel transfer procedures between transfer casks and storage casks. Such systems and methods are disclosed in U.S. Pat. No. 6,853,697, issued Feb. 8, 2005, to the assignee of the present application. However, such systems and methods are not ideal for performing the aspect of the transfer and/or work procedure wherein the radioactive payload needs to be lifted out of a shielding container and/or work needs to be performed within the cavity in which the radioactive payload is located. Thus, a needs exists for improved systems and methods

BRIEF SUMMARY OF THE INVENTION

In one embodiment, the invention can be a system for transferring a radioactive payload comprising: a first shielding container comprising a first cavity and a removable shielding lid, the radioactive payload located within the first cavity: a shield-gate apparatus comprising a body, a passageway extending along an axis through the body from a first opening in a top surface of the body to a second opening in a bottom surface of the body, and one or more movable shielding gates, the one or more shielding gates movable between: (1) a closed state in which the one or more shielding gates block the passageway; and (2) an open state in which the one or more shielding gates do not obstruct the passageway; the shield-gate apparatus positioned atop the first shielding container, the removable shielding lid having a bottom portion having a transverse cross-section that substantially corresponds to a transverse cross-section of the opening in the top surface of the body of the shield-gate apparatus in both size and shape.

In another aspect, the invention can he a system for facilitating work within a cavity of a first shielding container containing a radioactive payload, the system comprising: a shield-gate apparatus comprising a body, a passageway extending along an axis through the body from a first opening in a top surface of the body to a second opening in a bottom surface of the body, and one or more movable shielding gates, the one or more shielding gates movable between: (1) a closed state in which the one or more gates block the passageway; and (2) an open state in which the one Of more gates do not obstruct the passageway, the shield-gate apparatus positioned atop the first shielding container; a shielding block positioned atop the body of the shield-gate apparatus to enclose the first opening; and a retaining feature that prevents relative transverse movement between the shielding block and the shield-gate apparatus while allowing relative rotation between the shielding block and the shield-gate apparatus about a central axis of the shielding block.

In a further aspect, the invention can be a method of transferring a radioactive payload from a first shielding container to a second shielding container comprising: a) positioning a shield-gate apparatus atop the first shielding container, the shield-gate apparatus comprising a body, a passageway extending along an axis through the body from a first opening in a top surface of the body to a second opening in a bottom surface of the body, and one or more movable shielding gates; b) opening the one or more shielding gates of the shield-gate apparatus; c) lifting a removable shielding lid of the first shielding container through the passageway until the removable shielding lid is above the one or more shielding gates and closing the one or more shielding gates of the shield-gate apparatus; d) positioning a shielding block atop the shield-gate structure to enclose the first opening, the shielding block comprising a central axis and a first tool port offset from the central axis of the shielding block; e) removing a first shielding plug from the first tool port and opening the one or more shielding gates of the shield-gate apparatus; f) rotating the shielding block about the central axis of the shielding block to a first rotational position; g) inserting a first tool through the first tool port and removing one of a plurality of fasteners that secure a removable pressure vessel lid to a pressure vessel body using the first tool, the radioactive payload positioned within the pressure vessel; h) rotating the shielding block about the central axis from the first rotational position to a second rotational position; i) removing another one of the plurality of fasteners using the first tool; j) removing a second radiation shielding plug from a second tool port of the shielding block that is aligned with the central axis of the shielding block; k) inserting a second tool through the second tool port and lifting the pressure vessel lid through the passageway using the second tool until the pressure vessel lid contacts the shielding block; l) lifting both the shielding block and the removable pressure vessel lid using the second tool until the removable pressure vessel lid is above the one or more gates of the shield-gate apparatus and closing the one or more shielding gates of the shield-gate apparatus; k) positioning a second shielding container atop the shield-gate apparatus and opening the one or more shielding gates of the shield-gate apparatus; and l) lifting the radioactive payload through the passageway and into a second cavity of the second shielding container.

In still another aspect, the invention can be a method of providing access to a radioactive payload located within a first cavity of a first shielding container, the method comprising: a) positioning a shield-gate apparatus atop the first shielding container, the shield-gate apparatus comprising a body, a passageway extending along an axis through the body from a first opening in a top surface of the body to a second opening in a bottom surface of the body, and one or more movable shielding gates that are open; and b) lifting a removable shielding lid of the first shielding container through the passageway and closing the one or more shielding gates of the shield-gate apparatus, wherein the removable shielding lid is maintained in a position in which either: (1) a bottom surface of the removable shielding lid is disposed within the passageway at a height above the one or more shielding gates; or (2) the bottom surface of the removable shielding lid is substantially flush with the top surface of the body of the shield-gate apparatus, during the closing of the one or more shielding gates.

In yet another aspect, the invention can be a method of providing access to a radioactive payload located within a pressure vessel disposed within a first cavity of a first shielding container, the method comprising: a) positioning a shield-gate apparatus atop the first shielding container, the shield-gate apparatus comprising a body, a passageway extending along an axis through the body from a first opening in a top surface of the body to a second opening in a bottom surface of the body, and one or more movable shielding gates that are open; b) positioning a shielding block atop the shield-gate apparatus to enclose the first opening; c) inserting a tool through a tool port in the shielding block and engaging with the tool a removable pressure vessel lid that has been unfastened from a pressure vessel body; d) lifting the removable pressure vessel lid through the passageway until the removable pressure vessel lid contacts the shielding block with the tool; and e) lifting both the shielding block and the removable pressure vessel lid using the tool until the removable pressure vessel lid is above the one or more gates of the shield-gate apparatus and closing the one or more shielding gates of the shield-gate apparatus.

In an even further aspect, the invention can be a method of working within a first cavity of a first shielding container containing a radioactive payload, the system comprising: a) positioning a shield-gate apparatus atop the first shielding container, the shield-gate apparatus comprising a body, a passageway extending along an axis through the body from a first opening in a top surface of the body to a second opening in a bottom surface of the body, and one or more movable shielding gates that are open; b) positioning a shielding block atop the shield-gate apparatus to enclose the first opening, the shielding block comprising a tool port that is offset from an axis of rotation of the shielding block; c) inserting a tool through the tool port and into the first cavity; and d) rotating the shielding block relative to the first shielding container about the rotational axis from a first rotational position to a second rotational position, wherein the tool performs work at the first rotational position and at the second rotational position.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE DRAWINGS

The following description of the preferred embodiment(s) is merely exemplary in nature and is in no way intended to limit the invention, its application, or uses. While the invention is exemplified in FIGS. 1-19 as being used in conjunction with a radioactive payload in the form of a highly radioactive filter, the invention is not so limited and the invention can be used to transfer and/or perform work near any type of high level radioactive materials and/or low level radioactive materials, including without limitation vitrified waste, spent nuclear fuel, and canisterized radioactive materials.

Figure 1:
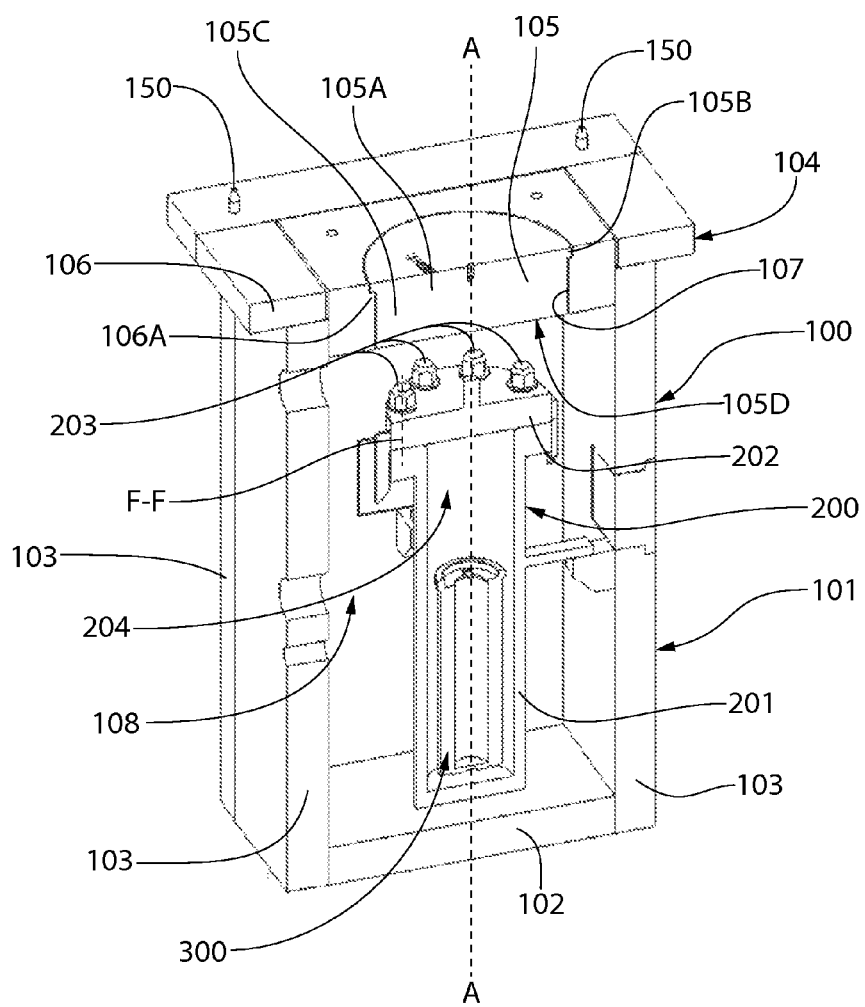
FIG. 1 is a cut-away view of a first shielding container having a pressure vessel containing a radioactive payload disposed therein according to an embodiment of the present invention.

Referring now to FIG. 1, a first shielding container 100 is exemplified according to an embodiment of the present invention is illustrated. In the exemplified embodiment, the first shielding container 100 is at filter box assembly. In alternate embodiments, the first shielding container 100 can be a storage cask, a transfer cask, or other shielding structure used to store and/or maintain radioactive materials (either temporarily or long-term). The first shielding container 100 is designed to provide the necessary amount of radiation shielding for the radioactive payload 300, thereby providing a radiation containment housing that protects the external environment and nearby workers from radiation emanating from the radioactive payload 300. Thus, in certain embodiments, the housing 101 of the first shielding container 100 is formed of a gamma radiation shielding material of engineered thickness. Suitable gamma radiation shielding materials include, without limitation, lead, steel, concrete, and combinations thereof. Furthermore, in alternate embodiments, the housing 101 of the first shielding container can include neutron absorbing materials to adequately contain neutron radiation.

The housing 101 of the first shielding container 100 comprises a floor slab 101, a plurality of upstanding wails 102 and a roof slab 103 that collectively form a first cavity 108 therein. The roof slab 104 comprises a removable shielding lid 105 that is removably mounted to a fixed portion 106 of the roof slab 104. In the exemplified embodiment, the removable shielding lid 105 comprises a plug portion 105A and a flange portion 105B. The removable shielding lid 105 comprises a bottom portion 105C (which is also the lowermost portion of the plug portion 105A in the exemplified embodiment). The removable shielding lid 105 also comprises a bottom surface 105D.

The removable shielding lid 105 is insertable into and encloses a central opening 107 (FIG. 7) in the roof slab 104. When inserted into the central opening 107, the flange portion 105B abuts against and contacts an annular shoulder 106A of the fixed portion 106, thereby supporting the removable shielding lid 105 in the central opening 107. As discussed above with respect to the other parts of the housing 101, the removable shielding lid 105 is formed a suitable radiation shielding material, such as a gamma radiation shielding material.

As discussed in greater detail below, the removable shielding lid 105 can be repetitively coupled and uncoupled from the fixed portion 106 of the roof slab 104. Moreover, as will be described in greater detail below, the fixed portion 106 of the roof slab 104 acts a landing structure that supports the gate shield apparatus 400 during transfer or work procedures. If desired, one or more fasteners can be utilized to secure the removable shielding lid 105 to the fixed portion 106 of the roof slab 104 in alternate embodiments. It should be noted that the housing 101 of the first shielding container 100 can take on a wide variety of structural configurations and shapes, none of which are limiting of the repent invention unless specifically claimed. For example, in one alternate embodiment, the removable shielding lid 104 can be coupled and uncoupled directly to the upstanding walls 103, without the need for a fixed portion 106. In such an embodiment, a portion of the upstanding walls 103 (or additional and separate structures) can be used to support the shield-gate structure 400 during transfer or work procedures.

The central opening 107 extends along an axis A-A, which is also a central axis of the housing 101 and the first cavity 108. In the exemplified embodiment, the axis A-A is oriented substantially vertical.

A pressure vessel 200 is disposed within the first cavity 104 of the first shielding container 100. The pressure vessel 200 comprises a pressure vessel body 201 and a removable pressure vessel lid 202 secured thereto by a plurality of fasteners 203. In the exemplified embodiment, the fasteners 203 are in the form of bolts. The invention, however, is not so limited in all embodiments and the fasteners 203 can take the form of screws, latches, locking cams, or other structures that can be used to secure lids to bodies. When the removable pressure vessel lid 202 is secured to the pressure vessel body 201, a hermetically sealed pressure vessel chamber 204 is formed. In the exemplified embodiment, the pressure vessel chamber 204 is hermetically isolated from the first cavity 108. Providing a hermetically sealable pressure vessel chamber 204 further protects the environment by creating a fluidic containment boundary about the radioactive payload 300, which is located within the pressure vessel chamber 204.

The pressure vessel body 201 and the removable pressure vessel lid 202 can be formed of materials, such as steel or other metals. Of course other suitable materials can be utilized. In the exemplified embodiment, the pressure vessel 200 does not provide the require radiation shielding for the radioactive payload 300 and, thus, the first shielding container 100 is required. Gaskets and other sealing techniques can he used between the pressure vessel body 201 and the removable pressure vessel lid 202 to form the desired hermetic sealing of the pressure vessel chamber 204.

The pressure vessel 200 comprises a central axis, which in the exemplified embodiment, is also axis A-A of FIG. 1. Thus, conceptually, the central axis of the pressure vessel 200 can be considered coaxial with the central axis of the opening 107 in the roof slab 104. In alternate embodiments, the central axis of pressure vessel 200 may be offset from the central axis of the central opening 107. The plurality of fasteners 203 are arranged in a circumferentially equi-spaced manner about the axis A-A. In the exemplified embodiment, each of the plurality of fasteners 203 are spaced from the axis A-A by the same distance. In the embodiment exemplified, each of the fasteners 204 can be considered to extend along a fastener axis F-F, which is substantially parallel to and spaced apart from the axis A-A by the same distance. Of course, the invention is not so limited in all embodiments.

In the exemplified embodiment, the radial distance between the fastener axes F-F and the axis A-A is less than the radius of the central opening 107. As a result, each of the fasteners 203 can be operated via the central opening 107 using a linear extension tool that remaining vertically oriented when the removable shielding lid 105 is removed therefrom.

Figure 2:
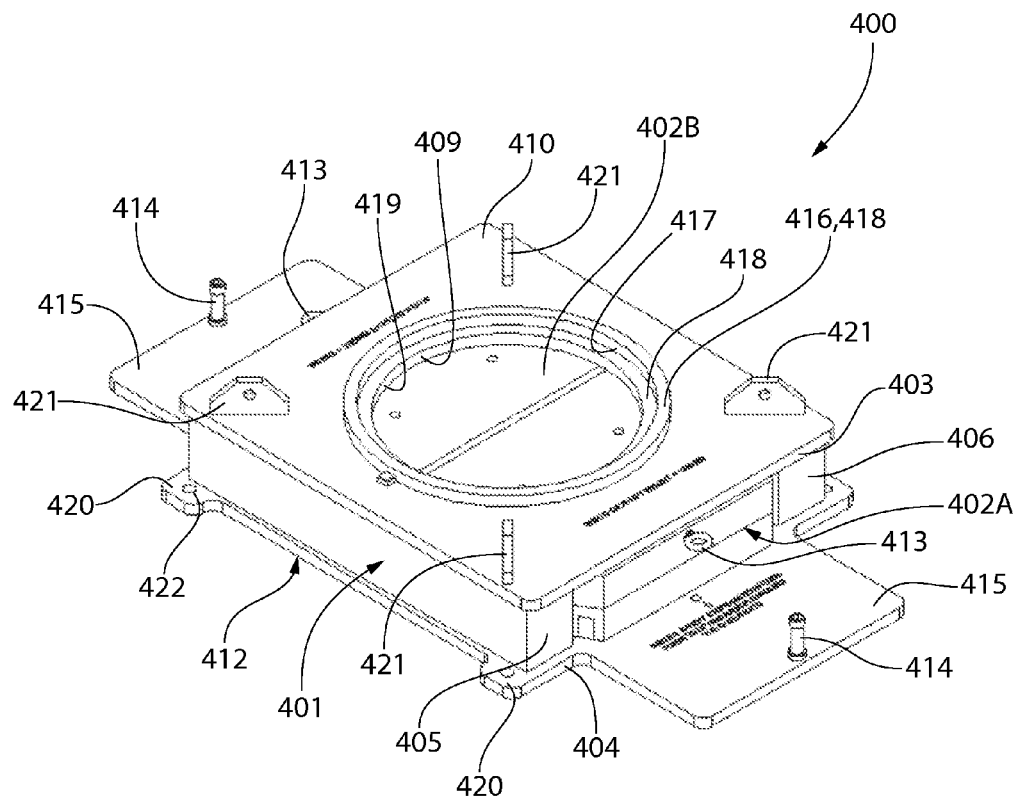
FIG. 2 is a top perspective view of a shield-gate apparatus according to an embodiment of the present invention, wherein the shielding gates are in a closed state.
Figure 3:
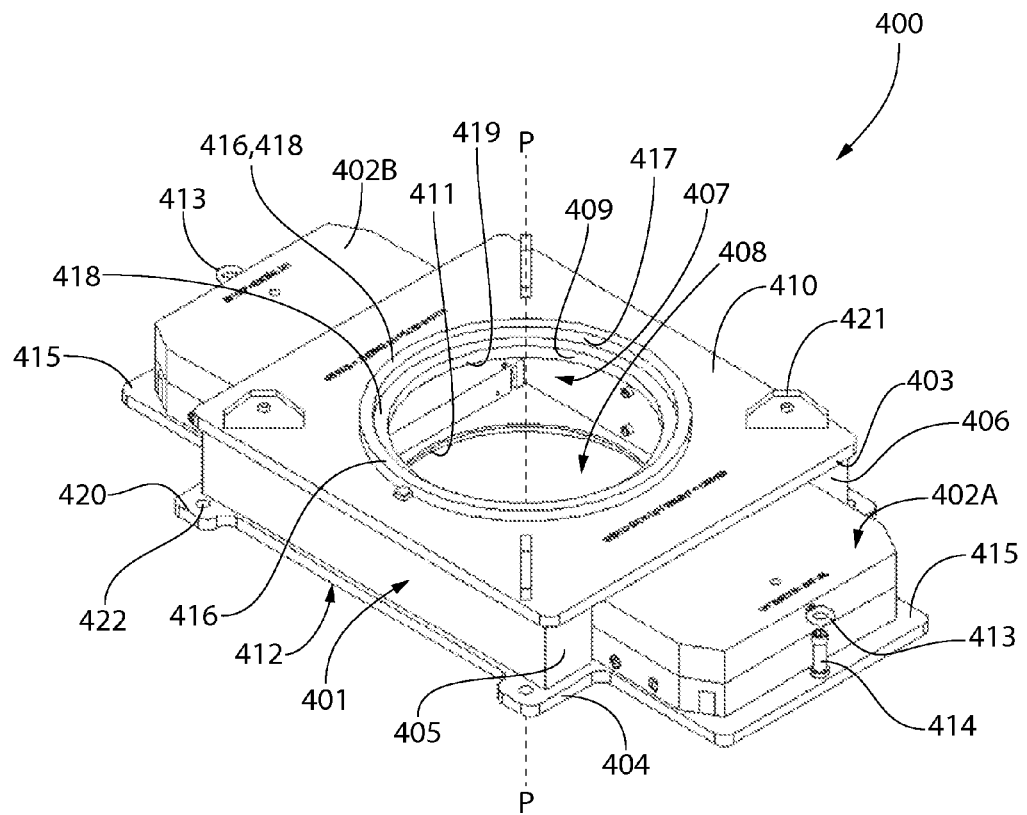
FIG. 3 is a top perspective view of a shield-gate apparatus according to an embodiment of the present invention, wherein the shielding gates are in an open state.

Referring now to FIGS. 2 and 3 concurrently, a shield-gate apparatus 400 according to one embodiment of the present invention is illustrated. The shield-gate apparatus 400 comprises a body 401 and two shielding gates 402A, 402B movable mounted within the body 401. The shielding gates 402A, B are thick structures designed to provide the required degree of radiation shielding to protect the environment and nearby workers from the radiation emitted by the radioactive payload 300 when the shielding gates 402A, 402B are used to enclose the central opening 107 of the housing 101 of the first shielding enclosure 100. As with the housing 101 of the first shielding container 100, the shielding gates 402A, 402B are formed of a gamma radiation shielding material of engineered thickness. Suitable gamma radiation shielding materials include, without limitation, lead, steel, concrete, and combinations thereof. Furthermore, in alternate embodiments, the shielding gates 402A, 402B can include neutron absorbing materials to adequately contain neutron radiation.

In the exemplified embodiment, the body 401 comprises a top plate 403, a bottom plate 404, a first wall plate 405, and a second wall plate 406. The first and second wall plates 405, 406 connect the top and bottom plates 403, 404 to form a gate chamber 407 in which the two shielding gates 402A, 402B are mounted. As with the shielding gates 402A, 402B, each of the plates 403-406 of the body 401 is formed of a gamma radiation shielding material of engineered thickness. Suitable gamma radiation shielding materials include, without limitation, lead, steel, concrete, and combinations thereof. Furthermore, in alternate embodiments, the shielding gates 402A, 402B can include neutron absorbing materials to adequately contain neutron radiation. As can be seen, the first and second side walls 405 are substantially thicker than the top and bottom plates 403, 404 because of they provide radiation shielding during transfer of the radioactive payload 300 through the shield-gate apparatus 400 (discussed below).

Each of the shielding gates 402A, 402B, are movable mounted to the body 401 (and within the gate chamber 407) so as to be alterable between: (1) a closed state (FIG. 2); and (2) an open state (FIG. 3). In the closed state, the shielding gates 402A, 402B block the passageway 408 (described below). In the open state, the shielding gates 402A, 402B do not obstruct the passageway 408. The passageway 408 extends along a central axis P-P. In the exemplified embodiment, the shielding gates 402A, 402B slidably translate relative to the body 401. In one embodiment, sliding between the shielding gates 402A, 402B and the body 401 can be accomplished by a suitably engineered low-friction interface between the body and the shielding gates 402A, 402B. In other embodiments, the sliding between the shielding gates 402A, 402B and the body 401 can be accomplished by rollers and/or slide track systems. When the shielding gates 402A, 402B are moved between the open state and the closed state, the shielding gates 402A, 402B move in opposite transverse directions (transverse to the central axis P-P). Hooks 413 are provided on the shielding gates 402A, 402B to provide a mechanism by which the shielding gates 402A, 402B can be grasped and moved between the open state and the closed state. Stoppers 414 are provided on the body 401, and specifically on the bottom plate 404, that prohibit the shielding gates 402A, 402B from being fully withdrawn from the gate chamber 407 and separated from the body 401. While the stoppers 414 are exemplified as posts, an protuberance or mechanical interference structure can be utilized. The stoppers 414 extend upward from transverse flanges 415 of the body 401, which are integrally formed with the bottom pate 404.

While two shielding gates 402A, 402B are used in the exemplified embodiment to seal and open the passageway 408, more or less shielding gates can be sued in alternate embodiments of the shield-gate apparatus 400. In certain embodiments, a single shielding gate can be used that covers the entirety of the passageway 408 in the closed state. Furthermore, while the shielding gates 402A, 402B are slidably mounted to the body 401 in the exemplified embodiment, the shielding gate(s) may be pivotable mounted to the body 401 in alternate embodiments so as to be pivotable between the open state and the closed state.

A first opening 409 is provided in the top surface 410 of the body and a second opening 411 is provided in the bottom surface 412 of the body 401. The passageway 408 extends through the body 401 from the first opening 409 to the second opening 411, thereby forming a pathway through which various components can be lifted through the shield-gate apparatus 400 (discussed below). Conceptually, the passageway 408 is formed by the first opening 409, the second opening 411 and that portion of the gate chamber 407 that is aligned with the first and second openings 409, 411.

The shield-gate apparatus 400 further comprises a retaining feature 416. As will be described in greater detail below, the retaining feature 416 is provided to prevent relative transverse movement between the shield-gate apparatus 400 and a component positioned atop the shield-gate apparatus 400 (such as the shielding block 500 and/or the second shielding container 600). As also discussed below, the retaining feature 416 prevents relative transverse movement between the shield-gate apparatus 400 and the component, while at the same time allowing relative rotation between the shield-gate apparatus 400 and the component about a rotational axis (such as the central axis P-P). The retaining feature 416 also allows the component to be separated from the shield-gate apparatus 400 by simply lifting the component in an axial direction away from the shield-gate apparatus 400.

In the exemplified embodiment, the retaining feature 416 comprises an inner side wall 417 of a retaining ring 418 that protrudes from the top surface 410 of the body 401. The inner side wall 417, in the exemplified embodiment, circumferentially surrounds the first opening 409 of the body 401 in a radially spaced apart manner. As a result, an annular ledge 418 is formed in the stop surface 410 between the first opening 409 and the inner side wall 417 of the retaining feature 416. While the retaining ring 418 is exemplified as a noninterrupted and continuous annular structure, in alternate embodiments, the retaining ring 418 can be segmented and discontinuous.

In other contemplated embodiments, the retaining feature 416 can take the form of properly positioned pegs (or protuberances) that protrude from the top surface 410 of the body in circumferentially spaced apart arrangement around the first opening 409. In still other embodiments, the retaining feature can be an outer side wall of a continuous annular groove formed into the top surface 410 of the body 401 that is either spaced from or adjacent the first opening 409. In such embodiments, the component (such as the shielding block 500 and/or the second shielding container 600) may comprise one or more protruding structures that slide axially into the groove for nesting therein. In even other embodiments, the retaining feature 416 can be the mere annular edge 420 (which acts as an upstanding side wall) that defines the first opening 409. In such embodiments, the component (such as the shielding block 500 and/or the second shielding container 600) may comprise a stepped surface that mates with the annular edge 419.

The shield-gate apparatus 400 further comprises a plurality of flanges 420 extending from the body 401 for securing the shield-gate apparatus 400 to the first shielding container 100. Lifting lugs 421 are also provided on the top surface 410 of the body 401 to facilitate engagement and lifting of the shield-gate apparatus 400 to position the shield-gate apparatus 400 atop the first shielding container 100.

Referring now to FIGS. 4-19, use of the shield-gate apparatus 400 to transfer the radioactive payload 300 form the first shielding container 100 to a second shielding container 600 will be described according to an embodiment of the present invention. During this discussion, additional components of the inventive system along with additional details of the structures discussed above will become apparent. Furthermore, while the invention will be described below with respect to the above-reference transfer procedure, it will become apparent to those skilled in the art that the structures and concepts discussed herein can be utilized to perform a wide variety of work in cavities that house radioactive payloads, while at the same protecting the external environment and nearby works from potential radiation shine.

Figure 4:
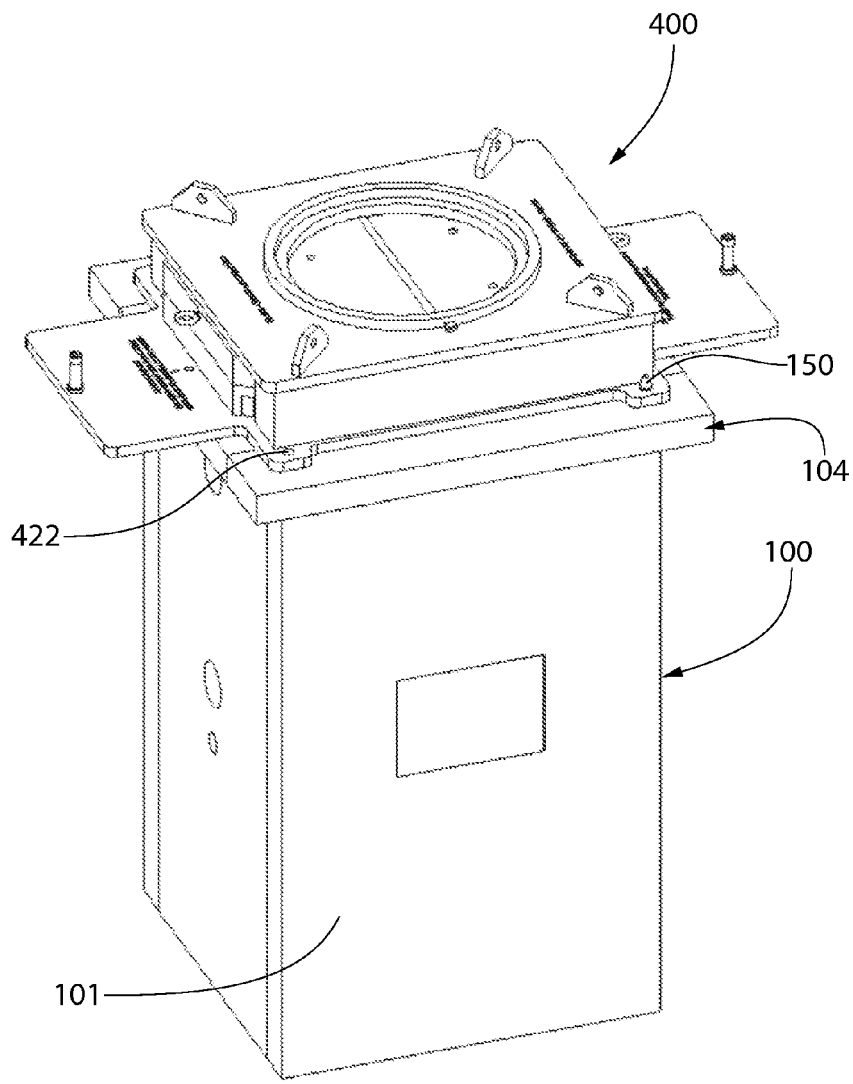
FIG. 4 is a top perspective view of the shield-gate apparatus of FIG. 2 positioned atop the first shielding container of FIG. 1 according to an embodiment of the present invention, wherein the shielding gates are in the closed suite.
Figure 5:
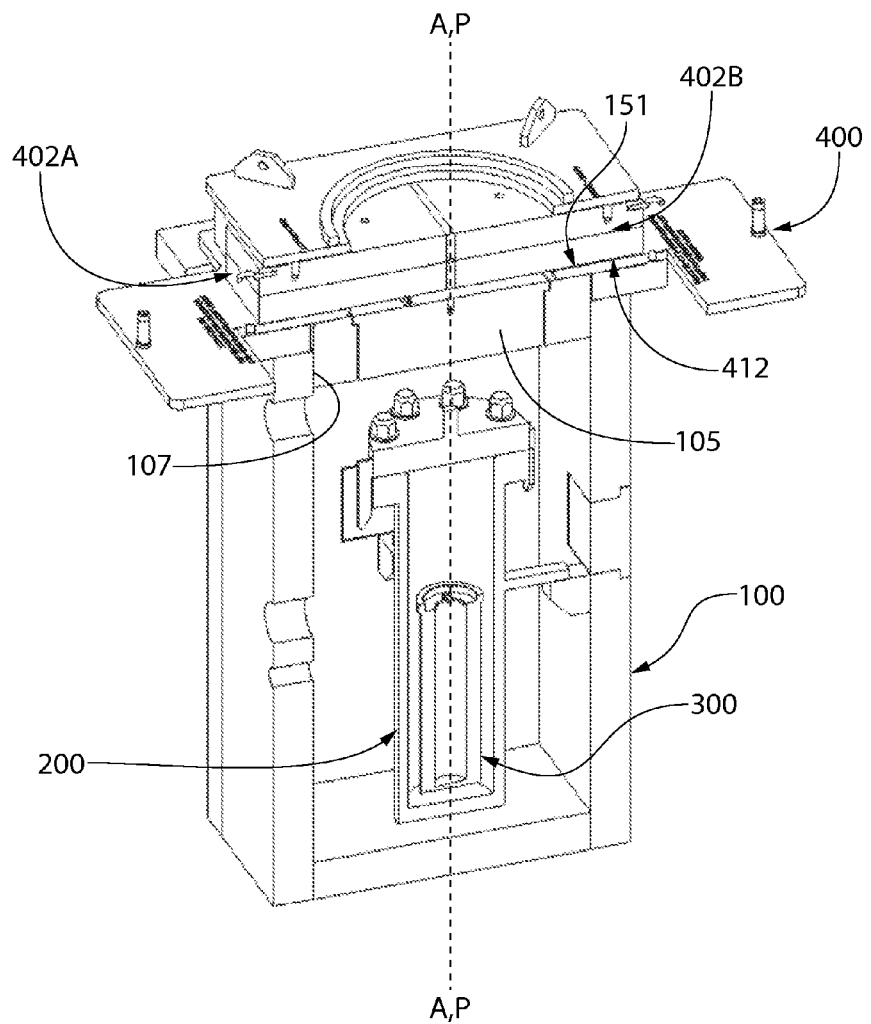
FIG. 5 is a top perspective view of the shield-gate apparatus positioned atop the first shielding container, as shown in FIG. 4, in partial cut-away and with the shielding gates in the closed state.

Referring specifically now to FIGS. 4 and 5 concurrently, the shield-gate apparatus 400 is first positioned atop the first shielding container 100. The bottom surface 412 of the shield-gate apparatus 400 is in surface contact with the top surface 151 of the first shielding container 100. The shield-gate apparatus 400 is positioned atop the first shielding container 100 in an alignment such that the central axis A-A of the central opening 107 is substantially coaxial with the central axis P-P of the passageway 408. Alignment pegs 150 that extend from the fixed portion 106 of the roof slab 104 of the first shielding container 100 extend through holes 422 (FIG. 3) of the flanges 420 of the shield-gate apparatus 400, thereby prohibiting relative transverse movement between the shield-gate apparatus 400 and the first shielding container 100. Alternatively, fasteners that extend through the holes 422 and into bores formed in the fixed portion 106 of the roof slab 104 can be used in addition to or instead of the alignment pins.

At this stage, the shielding doors 402A, 402B are in the closed state for ease of handling the shield-gate apparatus 400. However, in other embodiments, the shielding doors 402A, 402B may be in the open state if desired because the removable shielding lid 205 is still in place and seals the central opening 107 of the housing 101 of the first shielding container 100.

Figure 6:
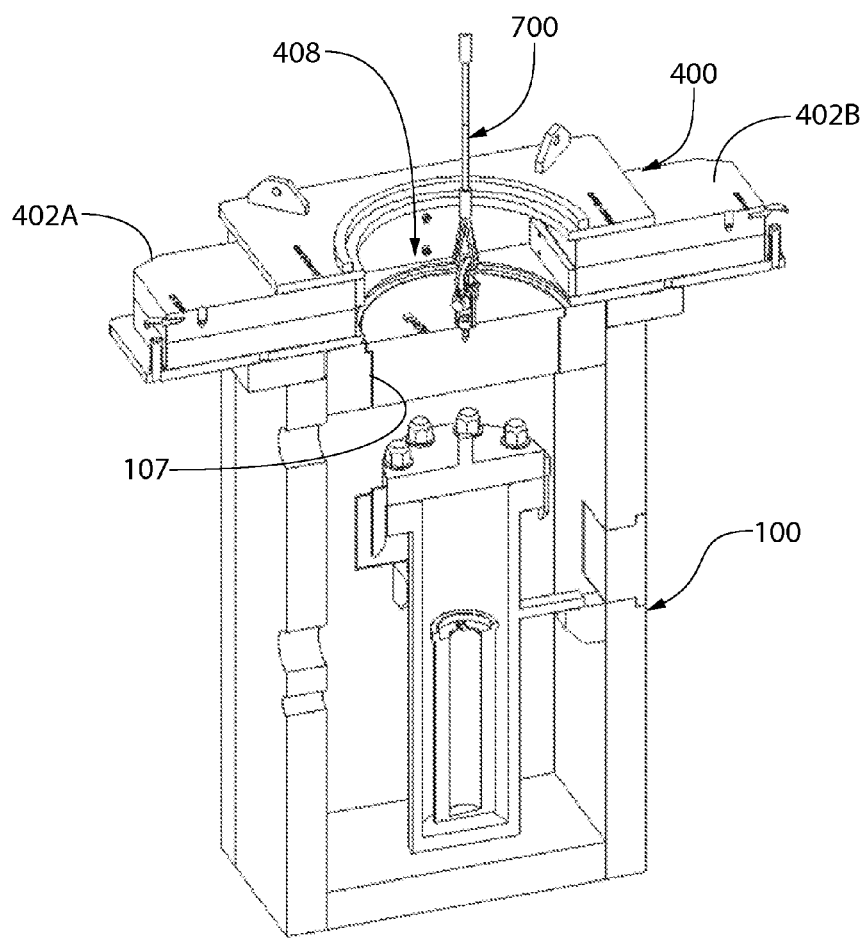
FIG. 6 is a top perspective view of a transfer/work system incorporating the shield-gate apparatus of FIG. 2 positioned atop the first shielding container of FIG. 1, wherein the shielding gates have been moved into an open state and wherein a tool, in the form of a lift rigging is attached to a removable shielding lid of the first shielding container.

Referring now to FIG. 6, once the shield-gate apparatus 400 is positioned atop the first shielding container 100 as described above, the shielding gates 402A, 402B of the shield-gate apparatus are moved from the closed-state to the open state (if not previously done so). As a result, the passageway 408 through the body 401 is unobstructed by the shielding gates 402A, 402B. A tool, in the form of a lifting rig 700, is then coupled to the removable shielding lid 105. The lifting rig 700, which is part of a larger crane or other lifting system, is then raised, thereby lifting the removable shielding plug 105 out of the central opening 107 (shown in FIG. 6) to a raised position in which the removable shielding lid 105 will not obstruct the shielding gates 402A, 402B from being moved back into the closed state (FIG. 7).

Figure 7:
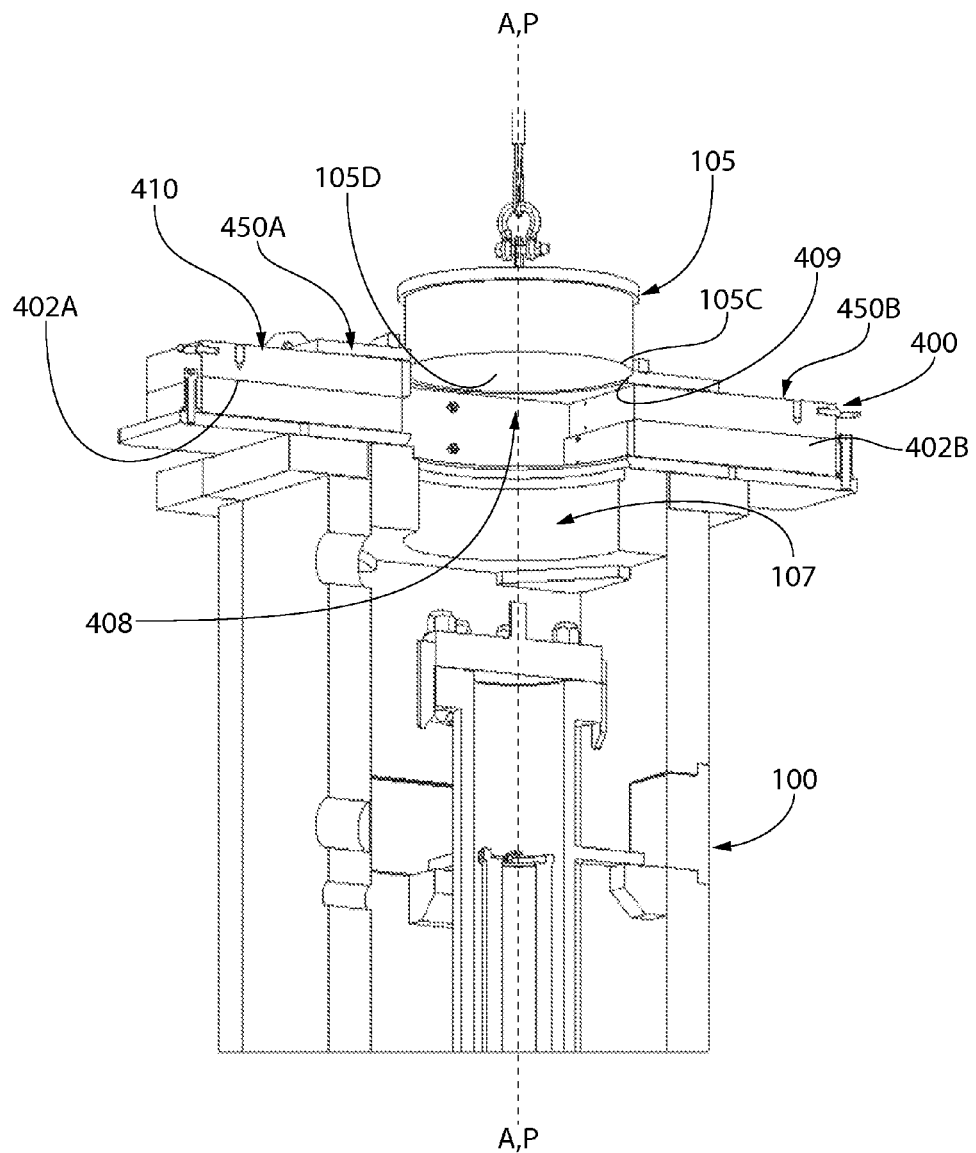
FIG. 7 is a bottom perspective view of the transfer/work system of FIG. 6, wherein the removable shielding lid of the first shielding container has been lifted through a passageway of the shield-gate apparatus to a position in which the removable shielding lid does not obstruct closing of the shielding gates while minimizing radiation escape from the cavity of the first shielding container.

Referring now to FIG. 7, the aforementioned raised position, and the benefits associated therewith, will be described in greater detail. When in the exemplified raised position, the bottom portion 105C of the removable shielding lid 105 remains within the passageway 408 of the shield-gate apparatus 400 while the bottom surface 105D of the removable shielding lid 105 is at an elevation (i.e., height) above the top surfaces 450A, 450B of the shielding gates 402A, 402B. Thought of another way, in the raised position, the bottom surface 105D of the removable shielding lid 105 is disposed within the passageway 408 at a height above the shielding gates 402A, 402B. Furthermore, the transverse cross-section of the first opening 409 of the passageway 408 substantially corresponds to the transverse cross-section of the bottom portion 105C of the removable shielding lid 105 in both size and shape. In one embodiment, the transverse cross-section of the first opening 409 of the passageway 408 is substantially the same as the transverse cross-section of the bottom portion 105C of the removable shielding lid 105 in both size and shape. Of course, a small tolerance must be provided for so that the removable shielding lid 105 does not get stuck in the first opening 409. In one embodiment, the tolerance is a relational value and is less 5% of the radius of the bottom portion 105D. In another embodiment, the tolerance is an empirical value and is less than 2 inches.

The removable shielding lid 105 is maintained in the aforementioned raised position until the shielding gates 402A, 402B are moved back into the closed state. By designing the first opening 409 to have a transverse cross-section that substantially corresponds to the transverse cross-section of the bottom portion 105C of the of the removable shielding lid 105 in both size and shape, and maintaining the removable shielding lid 105 in the aforementioned raised position, the removable shielding lid 105 itself prevents any substantial radiation shine to exit the passageway 408, despite the shielding gates 402A, 402B remaining open. In another embodiment, a suitable alternate raised position is achieved when the bottom surface 105D of the removable shielding lid 105 is substantially flush with the top surface 410 of the body 401 of the shield-gate apparatus 400.

Figure 8:
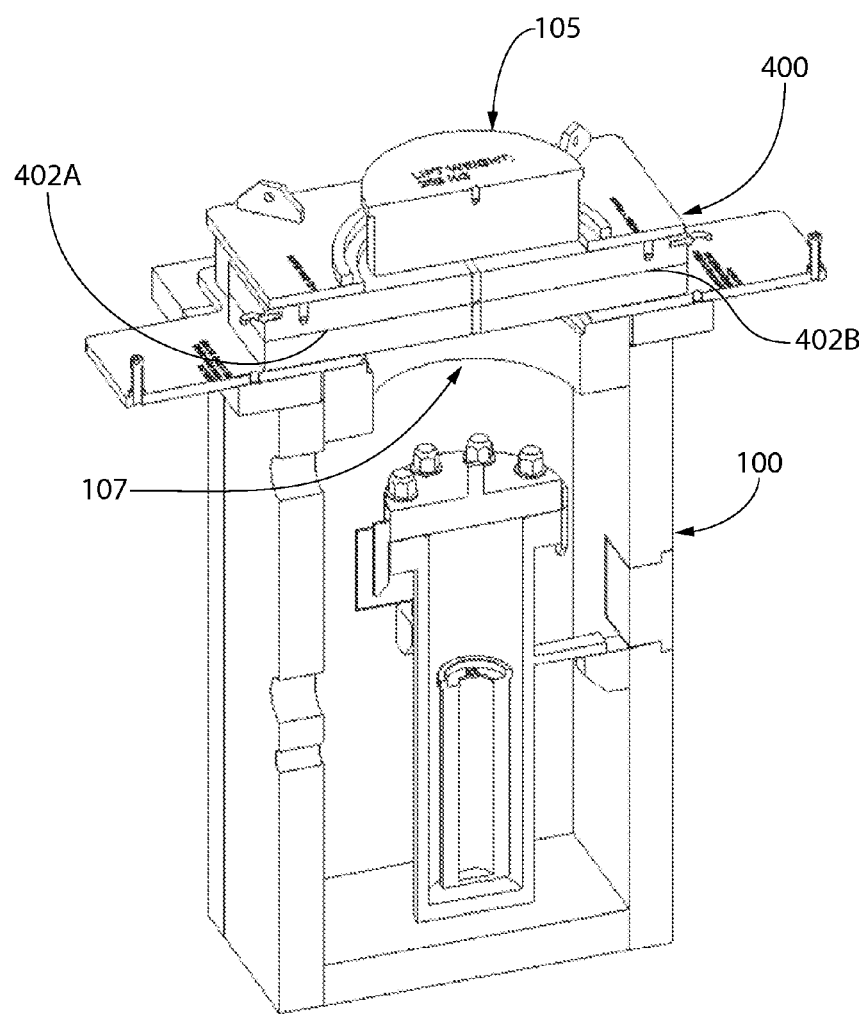
FIG. 8 is a top perspective view of the transfer/work system of FIG. 7, wherein the shielding gates have been moved to the closed state and support the removable shielding lid thereon.

Referring now to FIG. 8, once the removable shielding lid 105 is in the raised position shown in FIG. 7 (or the alternative raised position recited above), the shielding gates 402A, 402B moved into the closed state. The removable shielding lid 105 is then removed from the vicinity. Alternatively, it can be uncoupled from the lifting rig 700 and allowed to rest atop the shielding gates 402A, 402B until the next step in the procedure is ready in an effort to even farther improve radiation shielding.

Figure 9:
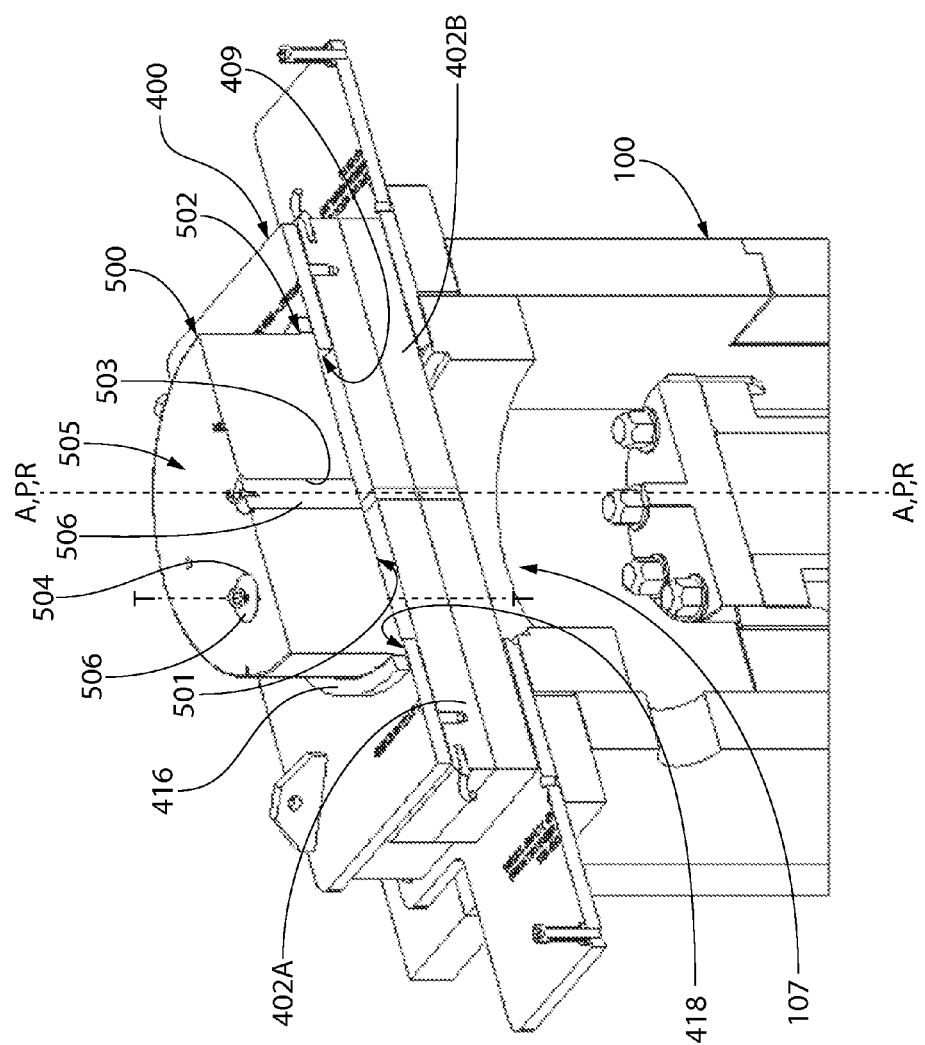
FIG. 9 is a top perspective view of the transfer/work system of FIG. 8, wherein the removable shielding lid has been removed and a shielding block has been positioned atop the shield-gate apparatus to enclose a first opening into the passageway of the shield-gate apparatus.

Referring now to FIG. 9, once the removable shielding lid 105 is out of the way, it is replaced by a shielding block 500. The shielding block 500 is positioned atop the shield-gate apparatus 400 to enclose the first opening 409. The shield block 500 is formed of a gamma radiation shielding material of engineered thickness. Suitable gamma radiation shielding materials include, without limitation, lead, steel, concrete, and combinations thereof. Furthermore, in alternate embodiments, the shielding gates 402A, 402B can include neutron absorbing materials to adequately contain neutron radiation. While the shielding gate 500 has a circular transverse cross-section in the exemplified embodiment, the shielding gate 500 can take on other shapes as desired in other embodiments.

The shielding gate 500 is positioned atop the shield-gate apparatus 400 such that mechanical interference between the shielding block 500 and the retaining feature 416 prevents relative transverse movement between the shielding block 500 and the shield-gate apparatus 400. Despite the existence of this mechanical interference that prevent relative lateral movement, the retaining feature 416 allows relative rotation between the shielding block 500 and the shield-gate apparatus 400 about a central axis R-R of the shielding block 500. Thus, in the exemplified embodiment, the central axis R-R of the shielding block 500 is also the axis of rotation. In other embodiments, the central axis R-R of the shielding block 500 can be offset from the axis of rotation. Furthermore, in the exemplified embodiment, the central axis R-R of the shielding block 500 (which is also the axis of rotation) is substantially coaxial with the axis A-A of the central opening 107 and the central axis P-P of the passageway 408 of the shield-gate apparatus 400. In alternate embodiments, one or more of the aforementioned axes may be offset from one another.

In the exemplified embodiment, the shielding block 500 is positioned atop the shield-gate apparatus 400 so that a perimeter portion of the bottom surface 501 of the shielding block 500 is in surface contact with the annular ledge 418 while a side surface 502 of the shielding block 500 is retained by the retaining feature 416. The shielding gates 402A, 402B are closed during the positioning of the shielding block 500 atop shield-gate apparatus.

The shielding block 500 comprises a plurality of tool ports 503, 504 that extend through the shielding block 500 from the top surface 505 to the bottom surface 501. The tool ports 503, 504 form vertical passageways through the shielding block 500 so that selected tools can be extended therethrough. In the exemplified embodiment, the shielding block 500 comprises a first tool port 504 that is offset a distance from the rotational axis of the shielding block 500 by a distance (which is also the central axis R-R in the exemplified embodiment). As discussed further below, the first tool port 504 has a tool port axis T-T that is spaced from the rotational axis R-R by a distance that is substantially the same as the distance by which the fastener axis F-F is spaced from axis A-A (FIG. 1). As a result, the shielding block 500 can be rotated about the rotational axis R-R so that the tool port axis T-T can be selectively oriented in substantially coaxial alignment with each of the fastener axes F-F. Thus, work can be performed through the first tool port 504 at a variety of circumferential locations. In the exemplified embodiment, the work is performed on the fasteners 203 and the tool part axis T-T is substantially parallel to the rotational axis R-R.

The shielding block 500 also comprises a second tool port 504 that is aligned with (i.e. coextensive) with the rotational axis of the shielding block 500 (which is also the central axis R-R in the exemplified embodiment). Of course, more or less tool ports can be provided in the shielding block 500 as necessary.

A shielding plug 506 is removably located within each of the first and second tool ports 503, 504. The shielding plugs 506 are formed of a gamma radiation shielding material as discussed above. The shielding plugs 506 are positioned within the tool ports 503, 504 to prevent unnecessary radiation escape when the tool port is not in use.

Figure 10:
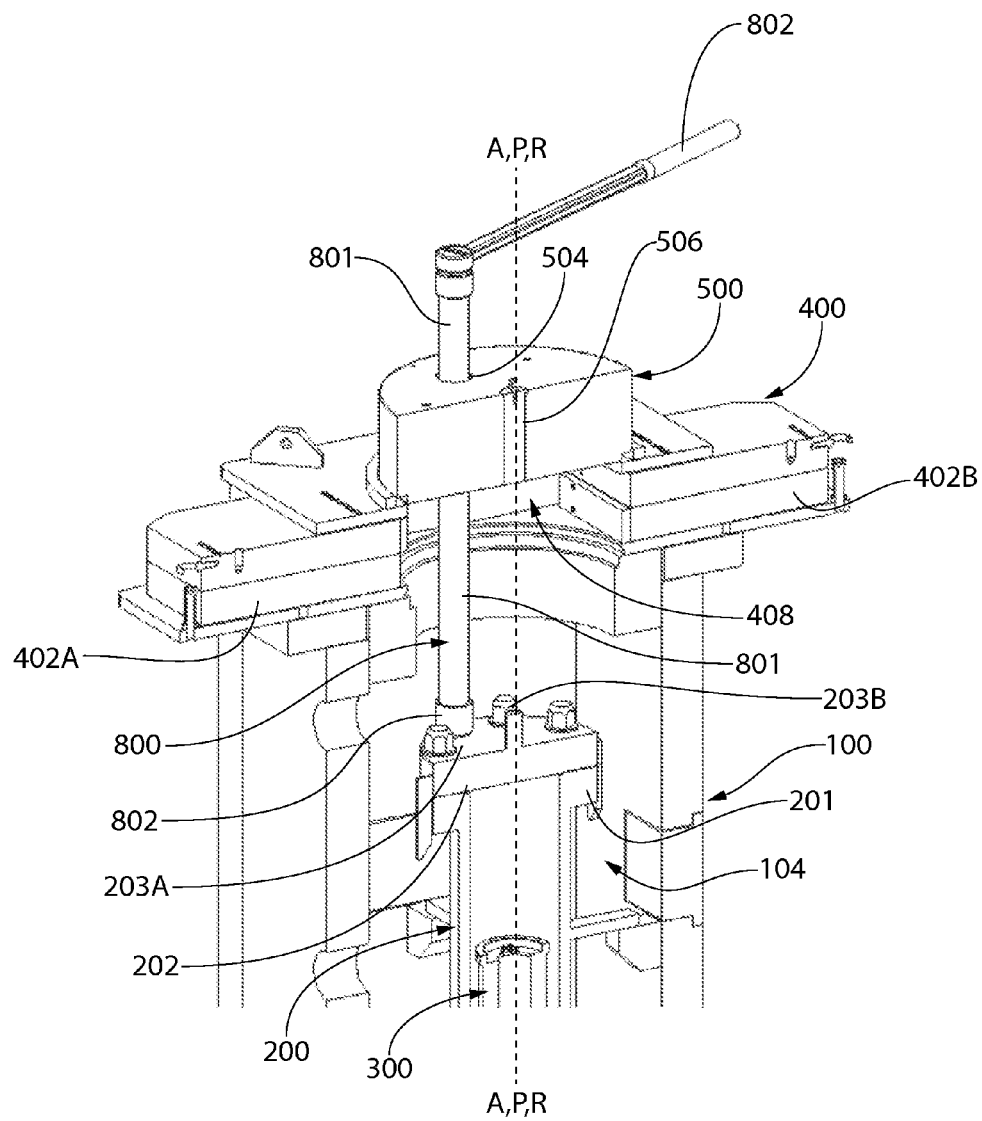
FIG. 10 is a top perspective view of the transfer/work system of FIG. 9, wherein the shielding block is positioned atop the shield-gate apparatus, the shielding gates have been moved into the open state, a tool in the form of an extension wrench has been inserted through an offset tool port of the shielding block.

Referring now to FIG. 10, once the shielding block 500 is in position atop the shield-gate apparatus 400 as discussed above, the shielding gates 402A, 402B are moved into the open state. As a result, the passageway 408 through the shield-gate apparatus is once again unobstructed. The shielding plug 506 is then removed front the first tool port 504, thereby providing an access pathway through the shielding block 500 so that work within the first cavity 104 can be performed by a tool, which in the exemplified embodiment is an extension wrench 800. The extension wrench has a shaft portion 801, head portion 802, and a control arm portion 803. The head portion 802 is inserted through the first tool port 504 and into the cavity 104 until it engages one of the fasteners 203A of pressure vessel 200. At this stage the shaft portion 801 extends from inside the first cavity 104 to outside of the system where it is coupled to the control arm portion 802. As shown in FIG. 10, the shielding block 500 is in a first rotational position such that the tool port axis T-T (see FIG. 9) is substantially coaxial with the fastener axis F-F (see FIG. 1) defined by the fastener 203A. As a result of this alignment, the head portion 802 of the extension wrench 800 can be fitted over the fastener 203A and subsequently rotated to unfasten and remove the fastener 203A from the pressure vessel 200. The shielding block 500 could have been positioned atop the shield-gate apparatus 400 so as to be already in the desired first rotational position, or the shielding block 500 may have been subsequently rotated into the first rotational position after initial placement.

Once the work is complete for fastener 203A, the shielding block 500 is rotated about the rotational axis R-R in either the clockwise or counterclockwise direction until the tool axis T-T of the first tool port 504 (FIG. 9) is substantially coaxial with the fastener axis F-F (FIG. 1) of another one of the fasteners 203B. The unfastening and removal process discussed above is then completed for this second fastener 203B. The aforementioned rotation and work sequence is repeated until all of the fasteners 203 are unfastened and removed, thereby freeing the removable pressure vessel lid 202 for removal from the pressure vessel body 201. Rotation of the shield block 500 can be performed with or without the extension wrench 800 remaining inserted through the first tool port 504.

Rotation of the shielding plug 500 can be achieved by a motor or other rotary mechanism that is either directly or indirectly coupled to the shielding plug 500. In one embodiment, rotation of the shielding plug 500 is accomplished by properly changing the orientation and/or position of the control arm portion 802 of the extension wrench 800. In such an embodiment, the motion of the control arm portion 802 is converted into rotation motion of the shielding block 500 via the shaft portion 801. In still other embodiments, separate control arms, pulleys, or linkages can be operably coupled to the shielding plug 500 at one end and operably coupled to a motor at a second end to achieve the desired rotary motion. In still other embodiments, a rotary platform can be placed into contact with the shielding block 500, or can be built therein. Other motion inducing forces are also contemplated, including magnetic attraction/repulsion that can be selectively activated through electrical current (i.e., electromagnets). In such an embodiment, properly positioned magnets will be positioned in the shielding plug 500 and along the gate-shield apparatus 400.

Figure 11:
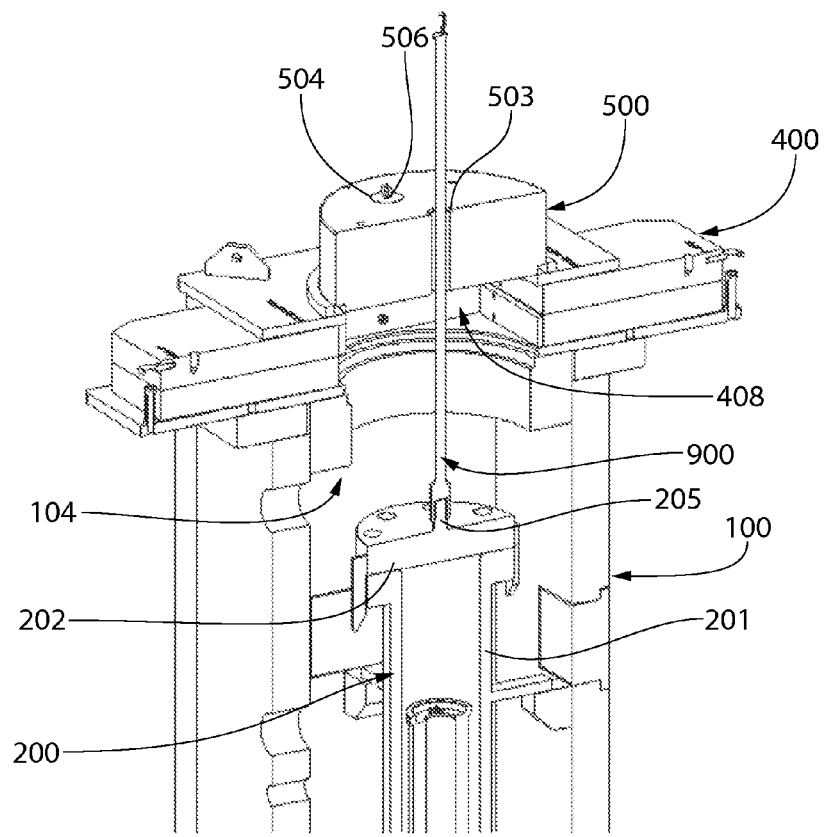
FIG. 11 is a top perspective view of the transler/work system of FIG. 10, wherein a shielding plug has been inserted into the offset tool port and a tool in the form of a grapple rod has been has been inserted through a central tool port of the shielding block to engage the removable pressure vessel lid of the pressure vessel.

Referring now to FIG. 11, once the fasteners 203 have all been properly removed, a shielding plug 506 is inserted into the first tool port 504 while the shielding plug 506 from the second toot port 503 is removed. Another tool, in the form of a grapple rod 900 is inserted through the second tool port 503 along the axis A-A until it engages a lifting lug 205 of the removable pressure vessel lid 202. Engagement between the grapple rod 900 and the lifting lug 205 can be accomplished through a threaded connection that is accomplished by rotating the grapple rod 900 about the axis A-A. As a result, the grapple rod 900 engages the removable pressure vessel lid 202 of the pressure vessel 200.

Figure 12:
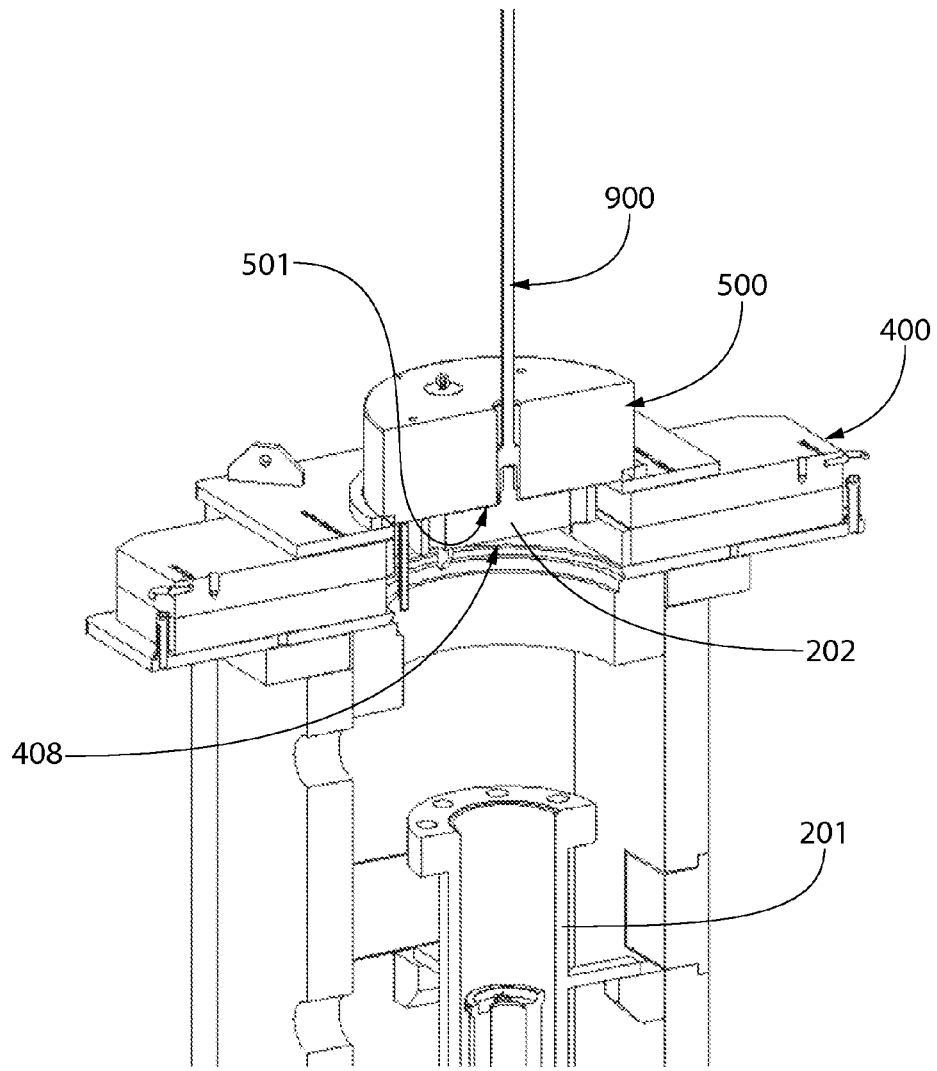
FIG. 12 is a top perspective view of the transfer/work system of FIG. 11, wherein the removable pressure vessel lid has been lifted by the grapple rod to contact a bottom surface of the shielding plug.

Referring now to FIG. 12, once the grapple rod 900 engages the removable pressure vessel lid 202, the removable pressure vessel lid 202 is lifted upward in the first cavity 104 until it passes into the passageway 408 of the shield-gate apparatus and contacts the bottom surface 502 of the shielding block 500. At this stage, the removable pressure vessel lid 202 is located within the passageway 408 of the shield-gate apparatus 400.

Figure 13:
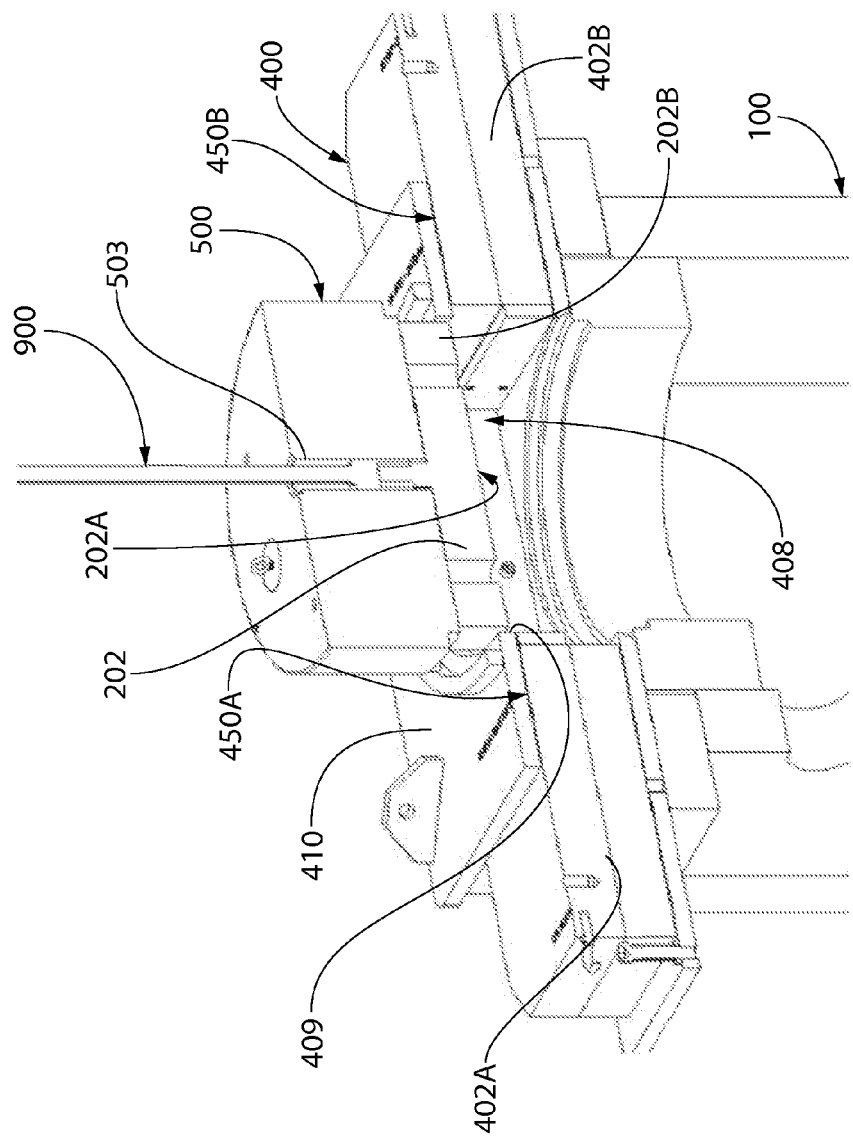
FIG. 13 is a top perspective view of the transfer/work system of FIG. 12, wherein the removable pressure vessel lid and the shielding plug have been lifted simultaneously by the grapple rod to a position in which the removable pressure vessel lid does not obstruct closing of the shielding gates while minimizing radiation escape from the cavity of the first shielding container

Referring now to FIG. 13, once the removable pressure vessel lid 202 contacts the bottom surface 502 of the shielding block 500, the grapple rod 900 continues to be raised. As a result, the removable pressure vessel lid 202 and the shielding block 500 are lifted upward. During this movement, the removable pressure vessel lid 202 acts as a flange (or washer) of the grapple rod 900 that engages the shielding block 500.

Figure 14:
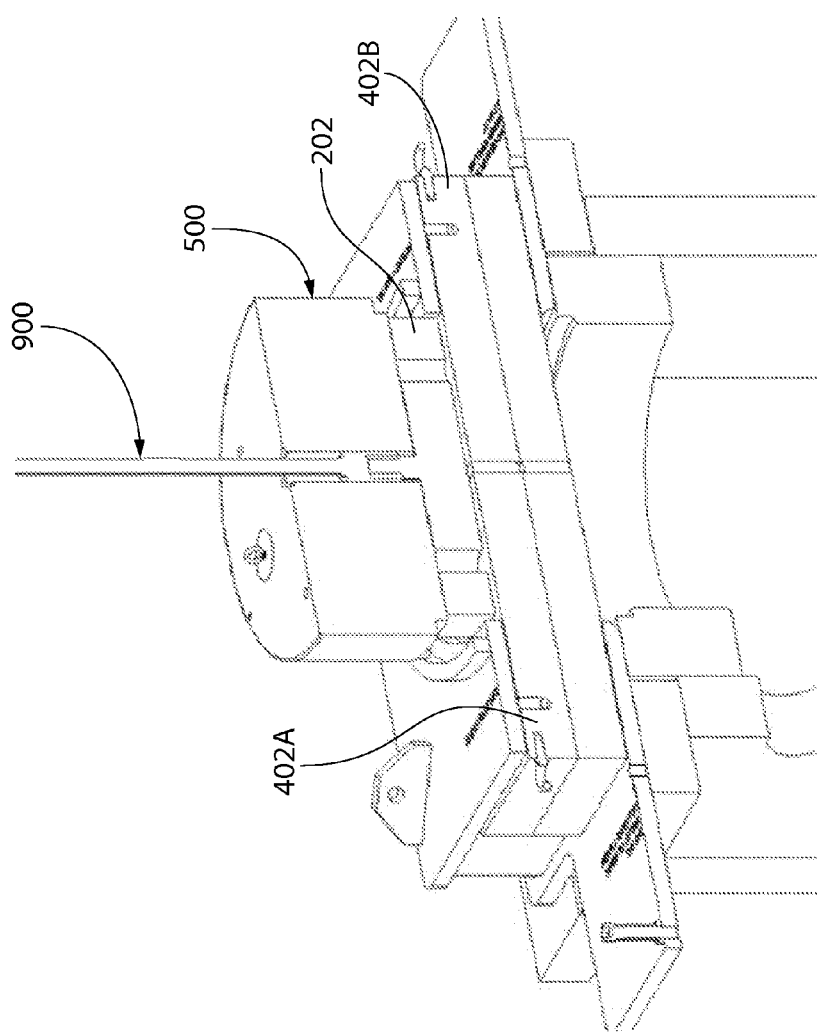
FIG. 14 is a top perspective view of the transfer/work system of FIG. 13, wherein the shielding gates have been moved in a closed-state.

Upward lifting of the combined removable pressure vessel lid 202 and shielding block 500 is continued until the raised position is achieved (illustrated in FIG. 13). In the raised position, neither the removable pressure vessel lid 202 nor the shielding block 500 will not obstruct the shielding gates 402A, 402B from being moved back into the closed state (FIG. 14). When in the exemplified raised position of FIG. 13, a bottom portion 202B of the removable pressure vessel lid 202 remains within the passageway 408 of the shield-gate apparatus 400 while the bottom surface 202A of the removable pressure vessel lid 202 is at an elevation (i.e., height) above the top surfaces 450A, 450B of the shielding gates 402A, 402B. Thought of another way, in the raised position, the bottom surface 202A of the removable pressure vessel lid 202 is disposed within the passageway 408 at a height above the shielding gates 402A, 402B. Furthermore, the transverse cross-section of the first opening 409 of the passageway 408 substantially corresponds to the transverse cross-section of the bottom portion 202B of the removable pressure vessel lid 202 in both size and shape. In one embodiment, the transverse cross-section of the first opening 409 of the passageway 408 is substantially the same as the transverse cross-section of the bottom portion 202A of the removable pressure vessel lid 202 in both site and shape. Of course, a small tolerance must be provided for so that the removable pressure vessel lid 202 does not get stuck in the first opening 409. In one embodiment, the tolerance is a relational value and is less 5% of the radius of the bottom portion 202A. In another embodiment, the tolerance is an empirical value and is less than 2 inches.

The removable pressure vessel lid 202 is maintained in the aforementioned raised position until the shielding gates 402A, 402B are moved back into the closed state. By designing the first opening 409 to have a transverse cross-section that substantially corresponds to the transverse cross-section of the bottom portion 202A of the of the removable pressure vessel lid 202 in both size and shape, and maintaining the removable pressure vessel lid 202 in the aforementioned raised position, the removable pressure vessel lid 202 itself helps prevents any substantial radiation shine to exit the passageway 408, despite the shielding gates 402A, 402B remaining open. In another embodiment, a suitable alternate raised position is achieved when the bottom surface 202A of the removable pressure vessel lid 202 is substantially flush with the top surface 410 of the body 401 of the shield-gate apparatus 400.

Referring now to FIG. 14, once the combined (and stacked) removable pressure vessel lid 202 and the shielding block 500 are in the raised position shown in FIG. 13 (or the alternative raised position recited above), the shielding gates 402A, 402B are moved into the closed state. The combined (and stacked) removable pressure vessel lid 202 and the shielding block 500 is then removed from the vicinity.

Figure 15:
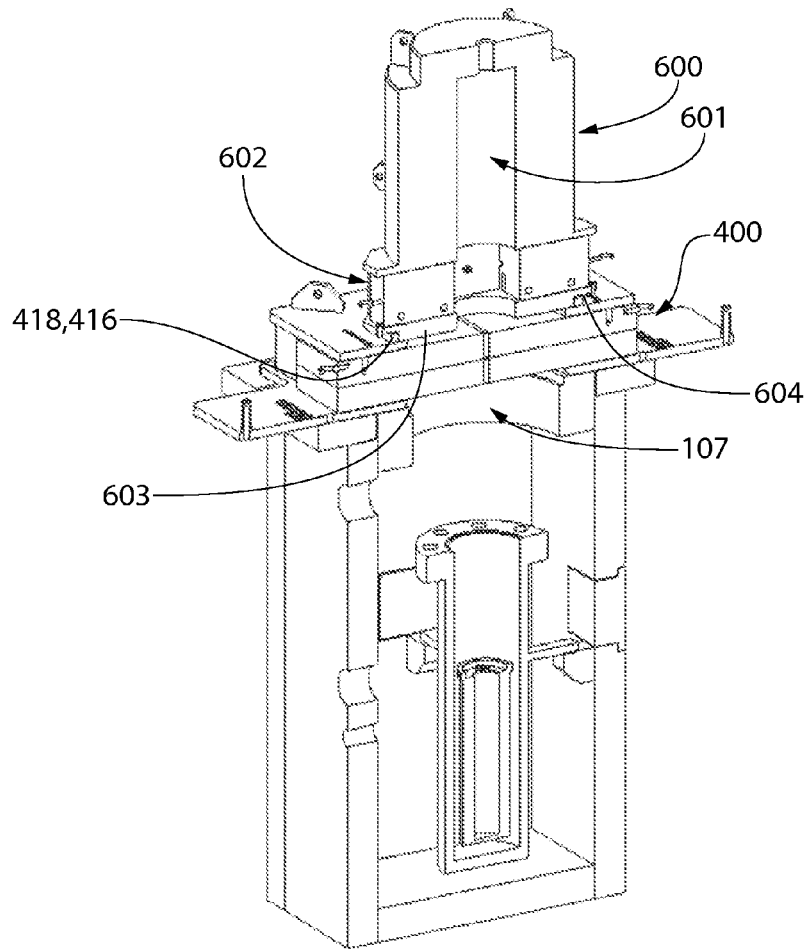
FIG. 15 is a top perspective view of the transfer/work system of FIG. 14, wherein the removable pressure vessel lid and the shielding plug have been removed and a second shielding container, in the form of a gated transfer cask has been positioned atop the shield-gate apparatus.

Referring now to FIG. 15, once the once the combined (and stacked) removable pressure vessel lid 202 and the shielding block 500 is out of the way, a second shielding container 200 is brought in. In the exemplified embodiment, the second shielding container 200 is in the form of a gated transfer cask 600. Other shielding containers can, of course, be used, including non-gated transfer casks. As with the first shielding container 100, the gated transfer cask 600 provides the required radiation shielding for the radioactive payload once it is transferred into the second cavity 601 of the gated transfer cask 600.

The gated transfer cask 600 comprises a transfer cask shield-gate 602 and a structure 603 protruding from a bottom surface 604 of the transfer cask shield-gate 602. The gated transfer cask 600 is first positioned atop the shield-gate apparatus 400 so that the second cavity 602 of the transfer cask in axial alignment with the first opening 409 of the shield-gat apparatus 400. When so aligned, the structure 603 of the gated transfer cask 600 protrudes into and nest within the retaining ring 418 of the shield-gate apparatus 400. As a result, the retaining ring 418 prevents relative transverse movement between the gated transfer cask 600 and the shield mite apparatus 400. The shielding gates 603A, 603B of the gated transfer cask are then moved into an open state, shown in PIG 15 (if not already in said open state). In certain embodiments, the gated transfer cask 600 may he secured to the shield-gate apparatus 400 via fasteners or other means.

Figure 16:
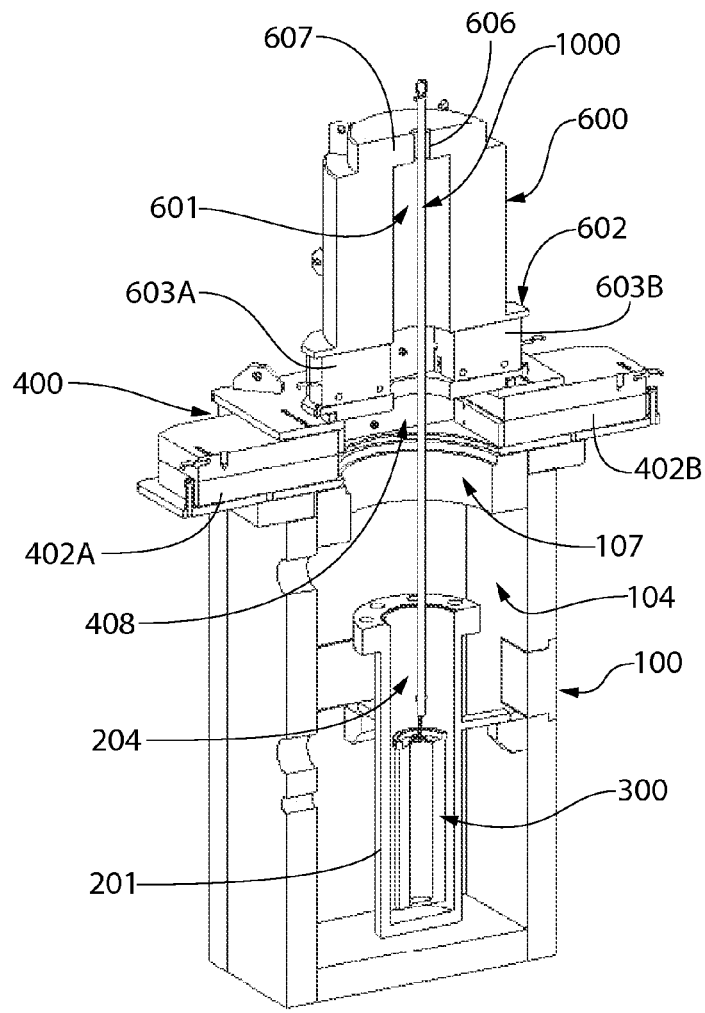
FIG. 16 is a top perspective view of the transfer/work system of FIG. 15, wherein the shielding gates of the gated transfer cask have been opened, the shielding gates of the shield-gate apparatus have also been moved into the open state, and a tool, in the form of a grapple rod has been inserted through the gated transfer cask to engage the radioactive payload, in the form of a filter.

Referring now to FIG. 16, once the gate transfer cask 500 is in position as described above, the shielding gates 402A, 402B of the shield-gate apparatus are moved back into the open state. As a result an unobstructed passageway is formed from the second cavity 601 of the gated transfer cask 600 all the way into the pressure vessel body 201 so that the radioactive load 300 can be manipulated. A grapple rod 1000 is then inserted through a port 606 in the lid 607 of the gated transfer cask 600. The grapple rod 1000 is lowered through the second cavity 602, through the passageway 408, through the central opening 107, through the first cavity 104, and into the open ended pressure vessel chamber body 204 where it engages the radioactive load 300. Engagement of the radioactive payload 300 can be accomplished in a variety manners, including achieving a threaded connection as discussed above.

Figure 17:
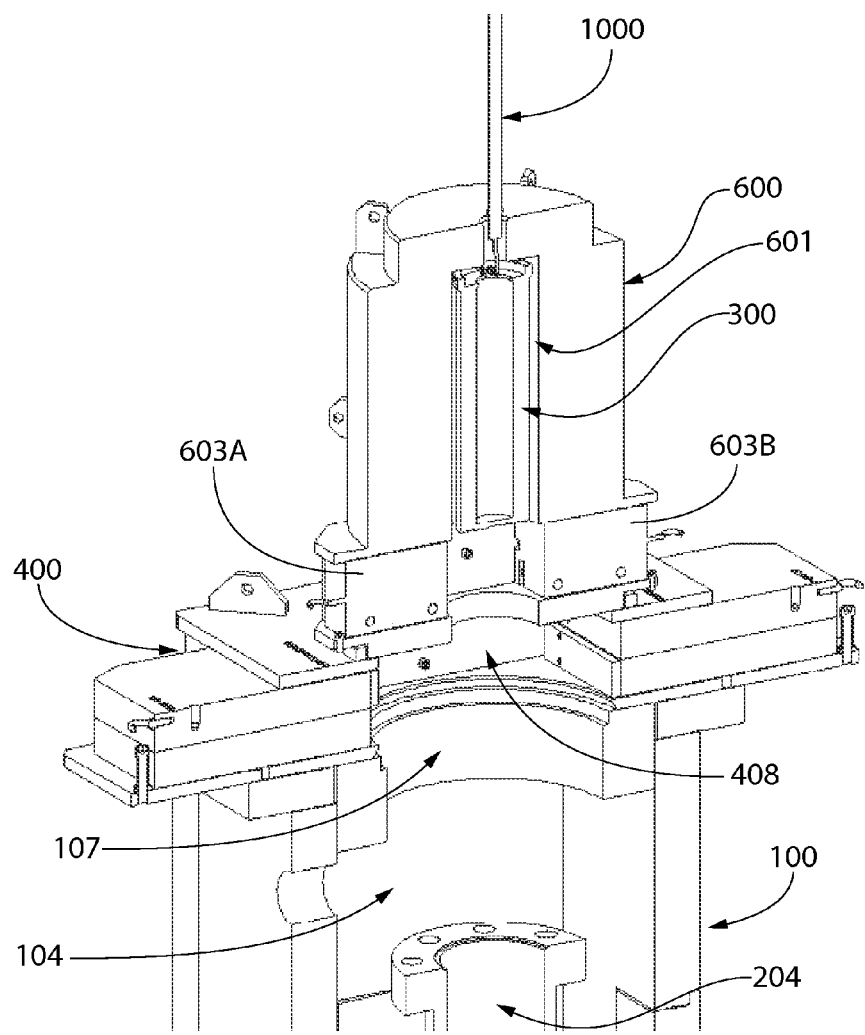
FIG. 17 is a top perspective view of the transfer/work system of FIG. 16, wherein the radioactive payload has been lifted by the grapple rod from the pressure vessel within the cavity of the first shielding container into a cavity of the gated transfer cask.
Figure 18:
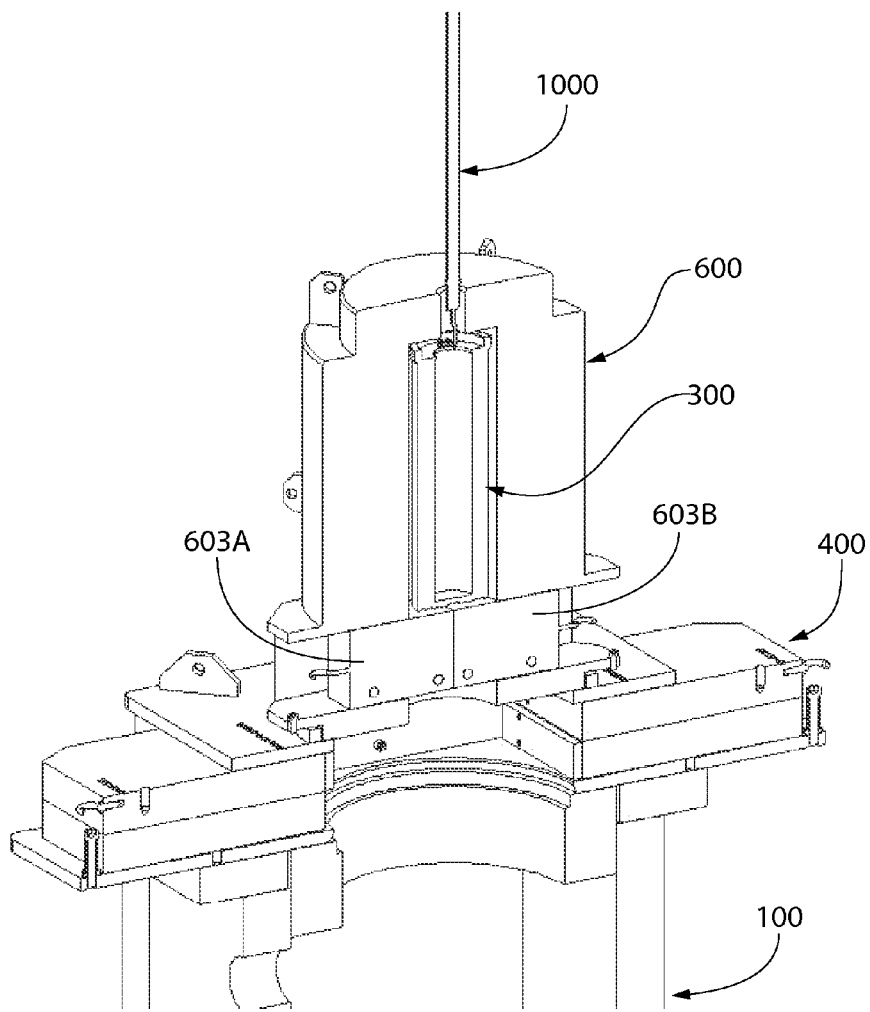
FIG. 18 is a top perspective view of the transfer/work system of FIG. 17, wherein the shielding gates of the gated transfer cask have been closed.
Figure 19:
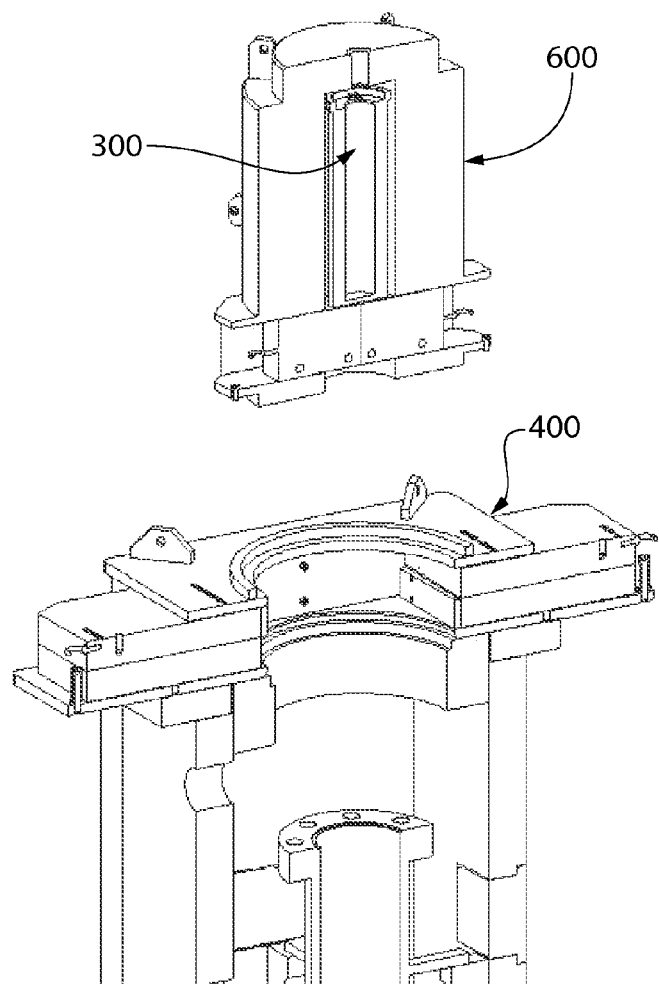
FIG. 19 is a top perspective view of the transfer/work system of FIG. 18, wherein the gated transfer cask has been lifted off the shield-gate apparatus.

Referring now to FIG. 17, once the radioactive payload 300 is engaged, the grapple rod 1000 is lifted upward so that the radioactive payload 300 passes out of the pressure vessel chamber 204, through the first cavity 104, through the central opening 107, through the passageway 408, and into the second cavity 602 of the gated transfer cask 600. The shielding gates 603A, 603B of the gated transfer cask 600 are then closed (FIG. 18), the grappling rod 1000 is uncoupled from the radioactive payload 300, and the gated transfer cask 600 (with its payload) is lifted off and away from the shield-gate apparatus 400.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilised and structural and functional modifications may be made without departing from the scope of the present invention. Thus, the spirit and scope of the invention should be construed broadly as set forth in the appended claims.

What is claimed is:

1. A system for transferring a radioactive payload comprising:
 a first shielding container comprising a first cavity and a removable shielding lid, the radioactive payload located within the first cavity;
 a shield-gate apparatus comprising a body, a passageway extending along an axis through the body from a first opening in a top surface of the body to a second opening in a bottom surface of the body, and one or more movable shielding gates, the one or more shielding gates movable between: (1) a closed state in which the one or more shielding gates block the passageway; and (2) an open state in which the one or more shielding gates do not obstruct the passageway;
 the shield-gate apparatus positioned atop the first shielding container, the removable shielding lid having a bottom portion having a transverse cross-section that substantially corresponds to a transverse cross-section of the opening in the top surface of the body of the shield-gate apparatus in both size and shape.

2. The system of claim 1 wherein the shield-gate apparatus comprises first and second shielding gates, the first and second shielding gates are slid in opposite transverse directions during movement between the open and closed states.

3. The system of claim 1 wherein the shield-gate apparatus comprises a top plate comprising the first opening, a bottom plate comprising the second opening, and first and second wall plates connecting the top and bottom plates to form a gate chamber in which the one or more gates are mounted.

4. The system of claim 1 wherein the shield-gate apparatus further comprises one or more flanges extending from the body for securing the shield-gate apparatus to the first container.

5. The system of claim 1 wherein the removable shielding lid is movable through the passageway between: (1) a first position in which the removable shielding lid is below the shield-gate apparatus and encloses an opening of the first cavity; and (2) a second position in which a bottom surface of the removable shielding lid is located within the passageway at a height above the one or more shield gates.

6. The system of claim 1 further comprising a shielding block, positioned atop the body of the shield-gate apparatus to enclose the first opening.

7. The system of claim 6 further comprising:
 the shielding block having a central axis that is substantially coaxial with the axis of the passageway; and
 a retaining feature that prevents relative transverse movement between the shielding block and the shield-gate apparatus while allowing relative rotation between the shielding block and the shield-gate apparatus about the central axis.

8. The system of claim 7 wherein the retaining feature comprises an inner side wall of a retaining ring that protrudes from the top surface of the body, the inner side wall of the retaining ring circumferentially surrounding the first opening of the body, the top surface of the body comprising an annular ledge that extends from the first opening to the inner side wall of the retaining ring, the shielding block in surface contact with and supported by the annular ledge.

9. The system of claim 7 wherein the shielding block comprises one or more tool ports extending through the shielding block and a removable shielding plug disposed within each of the one or more ports, and wherein at least one of the one or more tool ports is offset from the central axis of the shielding block.

10. The system of claim 9 wherein at least one of the one or more tool ports is aligned with the central axis of the shielding block.

11. The system of claim 9 further comprising:
 a pressure vessel positioned in the first cavity, the pressure vessel comprising a pressure vessel body and a removable pressure vessel lid secured to the pressure vessel body by a plurality of fasteners that are offset from a central axis of the pressure vessel, the radioactive payload disposed within the pressure vessel, the central axis of the pressure vessel substantially coaxial with the axis of the passageway;
 the plurality of fasteners spaced from the central axis of he pressure vessel by a first radial distance; and
 the at least one of the one or more tool ports offset from the central axis of the shielding block by a second radial distance that is substantially equal to the first radial distance.

12. The system of claim 1 further comprising:
 a transfer cask comprising a transfer cask shield-gate and a structure protruding from a bottom surface of the transfer cask shield-gate; and
 the shield-gate apparatus comprising a retaining feature that interacts with the structure to prevent relative transverse movement between the transfer cask and the shield-gate apparatus.

13. A system for facilitating work within a cavity of a first shielding container containing a radioactive payload, the system comprising:
 a shield-gate apparatus comprising a body, a passageway extending along an axis through the body from a first opening in a top surface of the body to a second opening in a bottom surface of the body, and one or more movable shielding gates, the one or more shielding gates movable between: (1) a closed state in which the one or more gates block the passageway; and (2) an open state in which the one or more gates do not obstruct the passageway, the shield-gate apparatus positioned atop the first shielding container;
 a shielding block positioned atop the body of the shield-gate apparatus to enclose the first opening; and
 a retaining feature that prevents relative transverse movement between the shielding block and the shield-gate apparatus while allowing relative rotation between the shielding block and the shield-gate apparatus about a central axis of the shielding, block.

14. The system of claim 13 wherein the shielding block comprises one or more tool ports extending through the shielding block and a removable shielding plug disposed within each of the one or more ports, and wherein at least one of the one or more tool ports is offset from the central axis of the shielding block.

15. The system of claim 14 further comprising a tool extending through the at least one of the one or more tool ports that is offset from the central axis of the shielding block.

16. The system of claim 15 further comprising means for rotating the shielding block about the central axis while the shielding block remains in surface contact with the shield-gate apparatus.

17. The system of claim 14 further comprising:
a pressure vessel positioned in the first cavity, the pressure vessel comprising a pressure vessel body and a removable pressure vessel lid secured to the pressure vessel body by a plurality of fasteners that are offset from a central axis of the pressure vessel, the radioactive payload disposed within the pressure vessel, the central axis of the pressure vessel substantially coaxial with the central axis of the shielding block;
the plurality of fasteners spaced from the central axis of the pressure vessel by a first radial distance; and
the at least one of the one or more tool ports offset from the central axis of the shielding block by a second radial distance that is substantially equal to the first radial distance.

18. The system of claim 14 wherein at least one of the one or more tool ports is aligned with the central axis of the shielding block.

19. The system of claim 13 wherein the retaining feature comprises an inner side wall of a retaining ring, that protrudes from the top surface of the body of the shield-gate apparatus, the inner side wall of the retaining ring circumferentially surrounding the first opening of the body, the top surface of the body comprising an annular ledge that extends from the first opening to the inner side wall of the retaining ring, the shielding block in surface contact with and supported by the annular ledge.

20. The system of claim 13 wherein the retaining feature comprises a side wall circumferentially surrounding the first opening of the body, an annular ledge extending from the first opening to the side wall, the shielding block in surface contact with and supported by the annular ledge.

* * * * *